United States Patent [19]

Shlain

[11] Patent Number: 5,263,927
[45] Date of Patent: Nov. 23, 1993

[54] APPARATUS AND METHODS FOR DISPENSING SURGICAL PACKING

[76] Inventor: Leonard M. Shlain, 40 Century Dr., Mill Valley, Calif. 94941

[21] Appl. No.: 939,267

[22] Filed: Sep. 2, 1992

[51] Int. Cl.⁵ .............................................. A61F 13/20
[52] U.S. Cl. ............................................ 604/13; 604/15; 604/51
[58] Field of Search ............................. 604/11–18, 604/51

[56] References Cited

U.S. PATENT DOCUMENTS

| | | |
|---|---|---|
| 636,637 | 11/1899 | Cooke . |
| 654,564 | 7/1900 | Dargatz . |
| 682,090 | 9/1901 | Lee . |
| 700,139 | 5/1902 | Fuller . |
| 702,997 | 6/1902 | Pugh . |
| 716,040 | 12/1902 | Holt . |
| 1,456,828 | 5/1923 | Pistor . |
| 1,537,257 | 5/1925 | Mizner . |
| 1,562,656 | 11/1925 | Park . |
| 2,524,195 | 10/1950 | Hoover ................... 604/13 |
| 4,610,659 | 9/1986 | Friese ..................... 604/11 |
| 4,895,559 | 1/1990 | Shippert ............. 604/904 X |
| 5,074,840 | 12/1991 | Yoon ..................... 604/15 |

Primary Examiner—Randall L. Green
Assistant Examiner—Mary Beth Jones
Attorney, Agent, or Firm—Townsend and Townsend

[57] ABSTRACT

A surgical packing dispenser comprises an elongate tube having a housing mounted on its proximal end. A continuous roll of sterilized packing material is disposed within the housing, and a free end of the packing material extends distally through the tube. The sterilized packing material is mounted on the spindle, and a handle is provided to rotate the spindle to feed material from the roll down the dispenser tube. In this way, relatively lengthy amounts of the packing material can be dispensed during laparoscopic and other endoscopic surgical procedures.

6 Claims, 4 Drawing Sheets

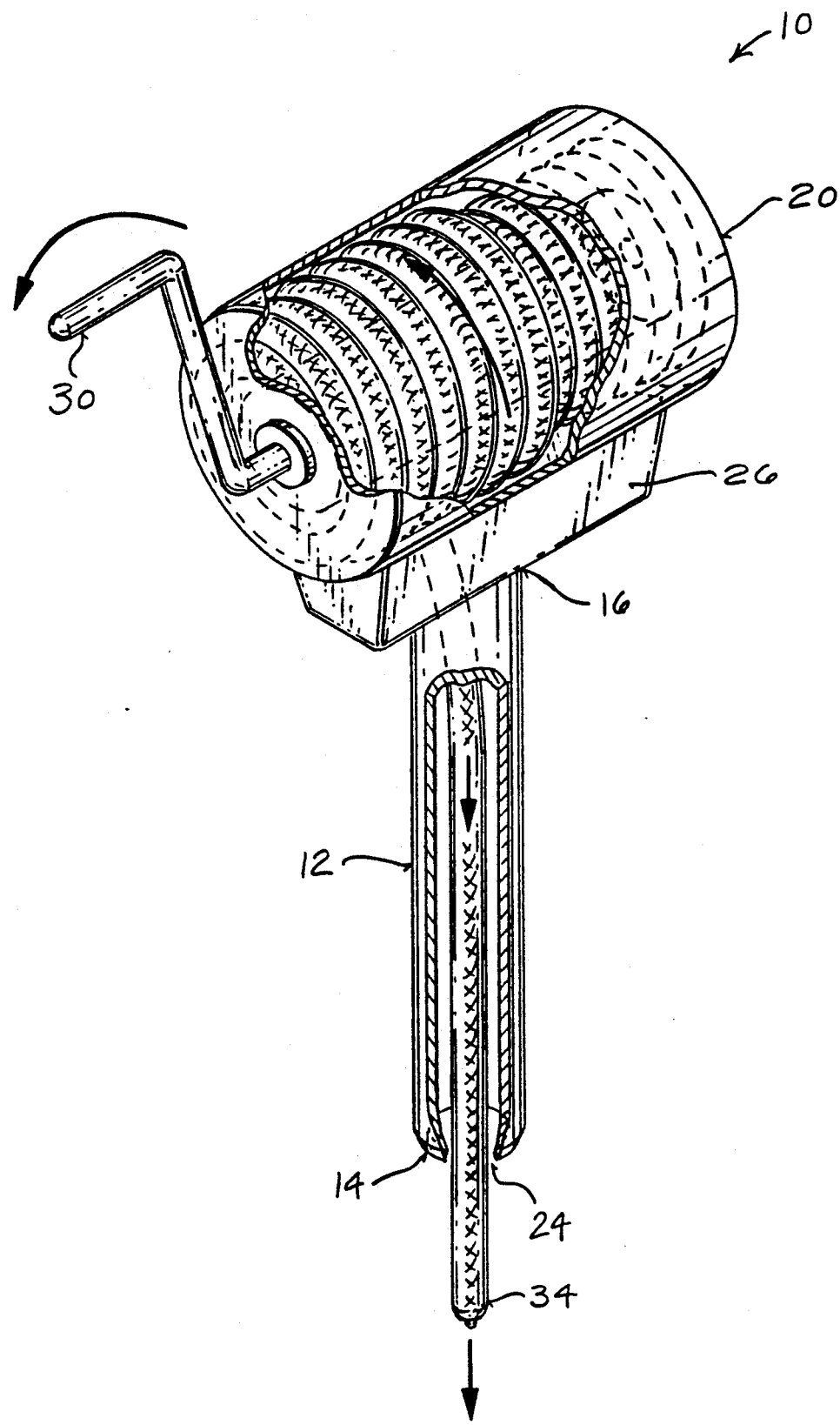
FIG_1A

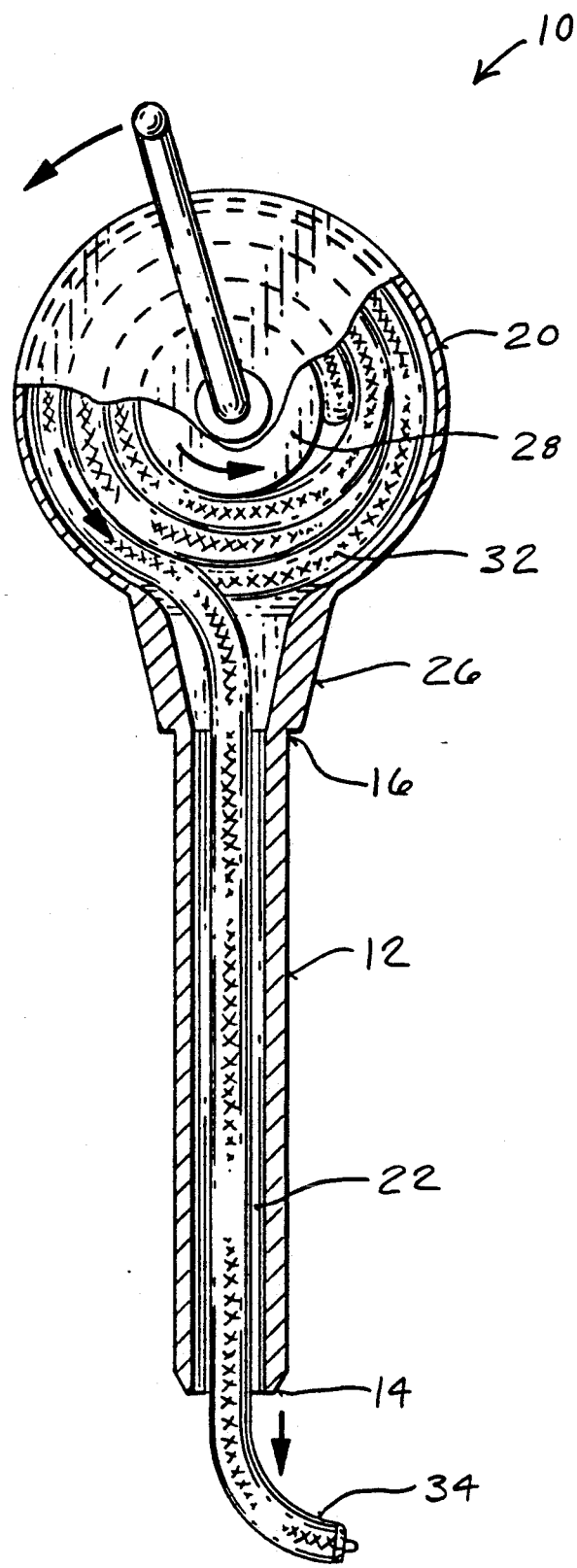
FIG_1B

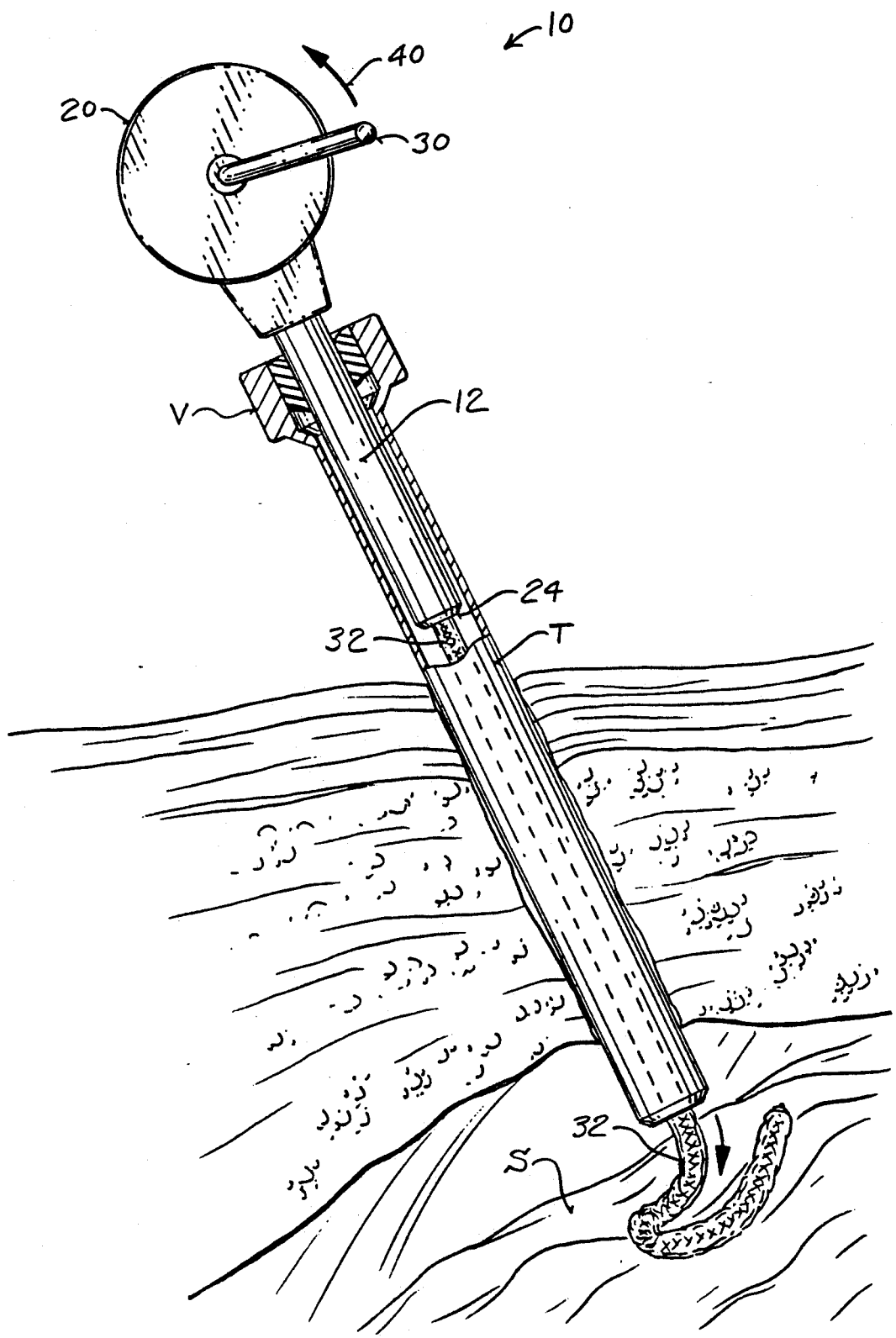
FIG_2

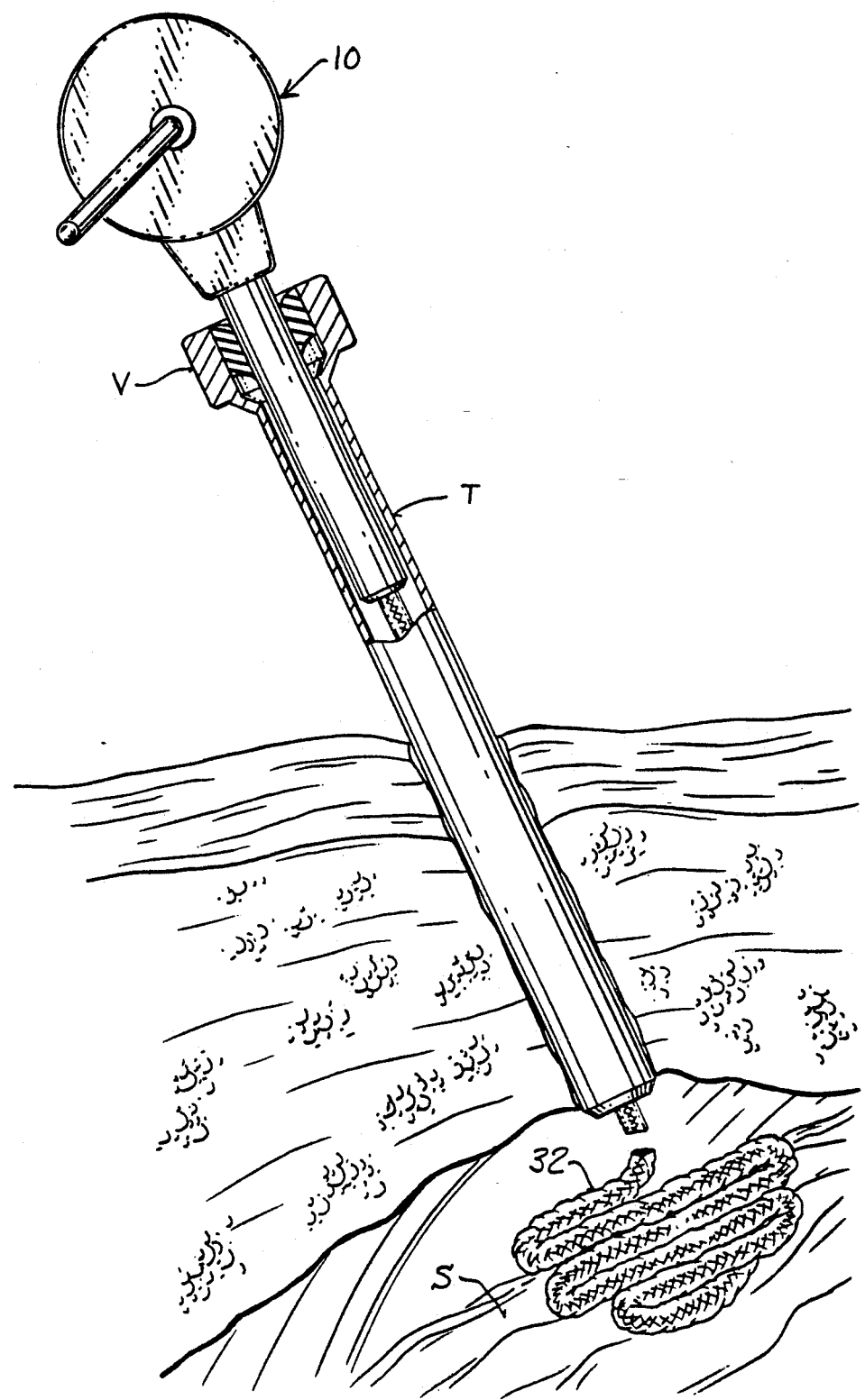
FIG_3

APPARATUS AND METHODS FOR DISPENSING SURGICAL PACKING

BACKGROUND OF THE INVENTION

1. Field of the Invention

The present invention relates generally to surgical apparatus and methods and, more particularly, to a device and method for dispensing surgical packing through a narrow diameter trocar.

Conventional open surgical procedures often use absorptive packing material, referred to as laptape, to pack organs away from the operating field and to staunch blood flow in areas of profuse bleeding. Laptape is generally composed of a soft cotton fabric and comes in various sizes, including small squares of about 15 inches and narrow strips of about 3 inches by 15 inches.

The use of laptape for surgical packing in laparoscopic and other endoscopic procedures is problematic. Laparoscopy relies on the use of narrow diameter access tubes, usually referred to as trocars, to provide access to a working region created by insufflation (pressurization) of a patient's abdominal region. The trocars have proximal valves, to maintain pressurization, and a laparoscope as well as certain specialized surgical instruments are introduced through several trocars to perform a desired surgical procedure. The introduction of conventional laptape through the trocars, however, is difficult or impossible.

Thus, there exists a need to provide devices and methods to facilitate the introduction and positioning of surgical packing during laparoscopy and other endoscopic procedures. The methods should permit the packing to be conveniently and accurately introduced through the laparoscopic trocars as a part of the surgical procedure.

U.S. Pat. No. 5,074,840, to Yoon, recognizes the difficulty in introducing conventional surgical packing material in laparoscopic and other endoscopic procedures. To overcome these difficulties, the '840 patent proposes using a relatively rigid strip of absorbent material which may be inserted directly through a trocar to a desired operative site. While initially rigid, the absorptive material softens when exposed to blood and other body fluids at the operative site. Optionally, a rigid delivery tube and rod assembly can be utilized to facilitate pushing the absorptive strip through the trocar.

The approach of the '840 patent suffers from certain drawbacks. In the first place, the use of a rigid rod limits the length of packing material that can be introduced through the trocar. Thus, it may be necessary to introduce two, three, or more individual strips in order to provide a sufficient mass of the absorptive material in a particular situation. Second, the positioning and manipulation of the rigid strips can be difficult. This is particularly true when multiple strips are necessary to provide a desired amount of absorptive material. Third, introduction of the rigid strips of absorptive material can sometimes compromise the pressurized seal which is being maintained by the proximal valve on the trocar. This is particularly true when multiple strips of material are to be introduced, although the problem can be ameliorated when using the tube and rod assembly for introducing the absorptive strips.

It would therefore be desirable to provide alternative and improved devices and methods for dispensing surgical packing in laparoscopic and other endoscopic surgical procedures. It would be particularly desirable if the devices and methods could dispense sufficiently long and continuous lengths of packing material so that the packing can usually be accomplished in a single step, i.e., without the need to introduce a plurality of separate packings. The methods and devices should also be easy to use and manipulate, and should provide a relatively tight seal when being introduced through the proximal valve of a trocar.

2. Description of the Background Art

U.S. Pat. No. 5,074,840, is described above. U.S. Pat. No. 2,524,195, describes a gauze packing device having a shaft with a roll of gauze disposed on one side. A push rod within the shaft can be used to advance gauze within the shaft. Other gauze and medical packing applicators are described in U.S. Pat. Nos. 4,895,559; 4,610,659; 1,562,656; 1,537,257; 1,456,828; 716,040; 702,997; 682,090; 654,564; 700,139; and 636,637.

SUMMARY OF THE INVENTION

According to the present invention, a surgical packing dispenser comprises an elongate tube having a proximal end and a distal end, and a housing mounted on the proximal end of the tube. A continuous roll of sterilized surgical packing material is disposed within the housing, and a free end of the packing material extends outwardly through the distal end of the elongate tube. A mechanism is provided for rotating the roll of packing material so that the free end of the packing material can be fed outwardly through the distal end of the elongate tube, typically with the assistance of a grasper inside the abdomen, in order to dispense the packing material at a desired target site.

According to the method of the present invention, the distal end of the elongate tube of the dispenser is positioned through the proximal end of the trocar so that the dispenser tube lies coaxially within the trocar and the distal end of the tube lies within the trocar shaft. In this way, as the roll of surgical packing material is rotated, the packing material will be pushed from the distal end of the dispenser tube into the interior lumen of the trocar. The packing material will subsequently pass through a distal length of the trocar and out through the distal trocar tip, to the target site of interest.

In the exemplary embodiment, the continuous roll of sterilized surgical packing material will be manually rotated, typically using a hand crank which turns a spindle upon which the packing material is wound. Alternatively, a motorized rotation mechanism can be provided, typically battery operated, so that the surgeon can both manipulate and actuate the dispenser using a single hand.

BRIEF DESCRIPTION OF THE DRAWINGS

FIG. 1A–1B illustrate a surgical packing dispenser constructed in accordance with the principles of the present invention. FIG. 1A is a perspective view. FIG. 1B is a side view, with portions broken away.

FIGS. 2 and 3 illustrate the use of the surgical packing dispenser of the present invention in dispensing a length of surgical packing to a target site through a trocar.

DESCRIPTION OF SPECIFIC EMBODIMENTS

Referring to FIG. 1A–1B, surgical packaging dispenser 10 comprises an elongate dispenser tube 12 having a distal end 14 and a proximal end 16. A housing 20 is secured to the proximal end of the dispenser tube 12, and the interior of the housing is open to axial lumen 22 of the tube 12. The tube 12 terminates in an open, distal aperture 24, but the remainder of the assembly of the tube 12 and housing 20 will generally be sealed to prevent contamination of packing material contained therein, as described in detail below.

The housing 20 is generally cylindrical and includes a transition region 26 which connects the cylindrical portion to the proximal end 16 of tube 12. A spindle 28 is located axially across the cylindrical portion of housing 20 and is secured at one end to a crank handle 30. The handle 30 is located outside of the housing 20 and the transition between the spindle 28 and handle passes through a sealed bearing surface to maintain isolation of the interior of the housing. The other end of the spindle 28 is mounted within an internal bearing within the housing.

A continuous roll of sterilized surgical packing material is wound over the spindle 28 to form a generally cylindrical roll which is positioned within the interior of the cylindrical portion of housing 20. A free end 34 of the surgical packing material 32 is initially disposed within the lumen of elongate tube 12, generally as illustrated in FIG. 1A. Rotation of the spindle 28 in the clockwise direction (as illustrated in FIG. 1B) using handle 30 will cause the free end 34 of the surgical packing to extend from the open distal aperture 24 of the tube 2, as illustrated in FIGS. 1B and 1C. Frequently, the packing material will be impregnated with an active substance, such as a clot promoter, an antibiotic, or the like.

The dimensions of the dispenser tube 12 will be selected to be introduced through a conventional trocar, typically a 10 mm trocar, of the type manufactured by U.S. Surgical Corp., Norwalk, CT. Usually, the dispenser tube 12 will have an outside diameter in the range from about 7.5 mm to 12.5 mm, typically being about 10 mm (to fit inside a standard 10 mm trocar). The length of the dispenser tube 12 will be sufficient to extend through the proximal valve of a trocar and into the main portion of the trocar tube, typically being in the range from about 10 cm to 20 cm, usually being about 15 cm.

The sterilized surgical packing material will be formed from a soft, absorbent fabric, typically being formed from rolled cotton cloth. The packing material will typically be in the form of a rope, usually having a length in the range from about 1.5 m to 3.0 m, usually in the range from about 1.8 m to 2.0 m. The material will have a diameter selected to fit within the interior lumen of dispenser tube 12, usually having a diameter from about 9.5 mm to 9.9 mm, typically being about 9.8 mm.

The surgical packing material will be wound over the spindle 28 in a series of reversing helically-coiled layers. The number of turns in each helical layer, and the number of layers, are not critical and will be selected to provide the desired length of the packing material. The spindle 28 will have a diameter sufficiently large so that enough peripheral force can be exerted on the end of the packing material to feed the packing material down the dispenser tube 12. Usually, the spindle 28 will have a diameter of at least about 1 cm, frequently being greater than 1.5 cm. Feeding of the packing material may be assisted by use of separate graspers which are introduced through a second trocar in place for the procedure.

Referring now to FIG. 2, the surgical packing dispenser 10 of the present invention will be inserted through a proximal valve V on a trocar T. The opened distal aperture 24 of the packing dispenser 10 terminates at a location well into the trocar lumen. After the packing dispenser 10 is in place, handle 30 will be rotated counterclockwise, as indicated by arrow 40, in order to dispense the packing material 32 distally down the lumen of trocar T. The packing material 32 will eventually be passed from the distal end of the trocar to the target site S, typically with the aid of a grasping instrument introduced through a separate trocar. The distal end of the trocar T can then be manipulated in order to position the resulting mass of packing material 32 as desired. After the desired amount of packing material 32 has been positioned, as illustrated in FIG. 3, the packing material will be cut, permitting the dispenser 10 to be withdrawn from the trocar T.

Although the foregoing invention has been described in detail for purposes of clarity of understanding, it will be obvious that certain modifications may be practiced within the scope of the appended claims.

What is claimed is:

1. A method for dispensing surgical packing, to a target site said method comprising:
   providing a dispenser having an elongate dispenser tube and a continuous roll of sterilized surgical packing material having a free end extending outward through a distal end of the tube;
   positioning the distal end of the elongate dispenser tube through a proximal end of a trocar so that a tube is coaxial with the trocar and the distal end of the tube lies within the trocar; and
   rotating the roll of sterilized packing material to feed the free end outward from the tube through a distal length of the trocar to the target site.

2. A method as in claim 1, wherein the distal end of the elongate tube is positioned under laparoscopic viewing.

3. A method as in claim 1, wherein the roll of sterilized packing material is manually rotated.

4. A method as in claim 1, wherein the continuous roll of sterilized surgical packing material is disposed on a spindle, and the roll is rotated by turning a crank attached to the spindle.

5. A method as in claim 1, further comprising cutting the surgical packing material near the distal end of the dispenser tube after a desired length of packing material has been dispensed, and removing the dispenser tube from the trocar.

6. A method as in claim 5, further comprising removing the cut length of packing material from the target site by pulling an end of the length through a trocar.

* * * * *